ized Cells through the Cell Cycle," *Analytical Biochem.* 141:70–73 (1984).

United States Patent [19]
Natarajan et al.

[11] Patent Number: 6,077,661
[45] Date of Patent: Jun. 20, 2000

[54] INTERNALLY CONTROLLED VIRION NUCLEIC ACID AMPLIFICATION REACTION FOR QUANTITATION OF VIRION AND VIRION NUCLEIC ACID

[75] Inventors: Venkatachala Natarajan, Germantown; Norman P. Salzman, Potomas, both of Md.

[73] Assignee: Georgetown University, Washington, D.C.

[21] Appl. No.: 08/949,333

[22] Filed: Oct. 14, 1997

Related U.S. Application Data

[63] Continuation of application No. 08/658,216, Jun. 4, 1996, abandoned, which is a continuation of application No. 08/258,288, Oct. 4, 1994, Pat. No. 5,814,442.

[51] Int. Cl.$^7$ .............................. C12Q 16/68; C12Q 1/70; C12P 19/34; C07H 21/04
[52] U.S. Cl. ................................ 435/5; 435/6; 435/91.1; 435/91.2; 536/23.1; 536/24.3
[58] Field of Search .......................... 435/5, 91.1, 320.1, 435/240.4, 240.2, 172.3, 235.1; 536/23.1, 24.3; 424/93 R

[56] References Cited

U.S. PATENT DOCUMENTS

| | | | |
|---|---|---|---|
| 4,356,270 | 10/1982 | Itakura | 435/317 |
| 4,458,066 | 7/1984 | Caruthers et al. | 536/27 |
| 4,683,195 | 7/1987 | Mullis et al. | 435/6 |
| 4,683,202 | 7/1987 | Mullis | 435/91 |
| 4,927,628 | 5/1990 | Chanock et al. | 424/89 |
| 5,180,666 | 1/1993 | States et al. | 435/29 |
| 5,183,949 | 2/1993 | Kindt et al. | 800/2 |
| 5,256,545 | 10/1993 | Brown et al. | 435/69.1 |
| 5,262,311 | 11/1993 | Pardee et al. | 435/91.2 |
| 5,278,056 | 1/1994 | Bank et al. | 435/172.3 |
| 5,334,498 | 8/1994 | Roizman et al. | 435/5 |
| 5,352,596 | 10/1994 | Cheung et al. | 424/205.1 |
| 5,378,605 | 1/1995 | Feitselon et al. | 435/5 |
| 5,521,291 | 5/1996 | Curiel et al. | 530/391.7 |
| 5,789,153 | 8/1998 | Falkner et al. | 435/5 |
| 5,795,722 | 8/1998 | Lacroix et al. | 435/6 |
| 5,814,442 | 9/1998 | Natarajan | 435/5 |

FOREIGN PATENT DOCUMENTS 0 373 960 A2   6/1990   European Pat. Off. .......... C12Q 1/68

OTHER PUBLICATIONS

Baudin et al J. Mol. Biol. vol. 229 pp. 382–397, 1993.
Castrucci et al J. of Virol vol. 66, No. 8, pp. 4647–4653, 1992.
Glazenburg et al Vaccine vol. 12 No. 12 pp. 1097–1100, 1994.
Clementi et al PCR Methods and Application vol. 2 pp. 191–196, 1993.
Adachi, A. et al., "Production of Acquired Immunodeficiency Syndrome–Associated Retrovirus in Human and Nonhuman Cells Transfected with an Infections Molecular Clone," *J. Virol.* 59(2):284–291 (1986).

Aoki–Sei, S. et al., "Plasma HIV–1 Viremia in HIV–1 Infected Individuals Assessed by Polymerase Chain Reaction," *Aids Res. Human Retrov.* 8(7):1263–1270 (1992).
Bagnarelli, P. et al., "Detection of Human Immunodeficiency Virus Type 1 Genomic RNA in Plasma Samples by Reverse–Transcription Polymerase Chain Reaction," *J. Med. Virol.* 34:89–95 (1991).
Barany, F., "Genetic disease detection and DNA amplification using cloned thermostable ligase," *Proc. Natl. Acad. Sci. USA.* 88:189–193 (1991).
Beaucage, S. L., and M. H. Caruthers, "Deoxynucleoside Phosphoramidites —A New Class of Key Intermediates for Deoxypolynucleotide Synthesis," *Tetrahedron Letts.* 22(20):1859–1862 (1981).
Becker–André, M. and K. Hahlbrock, "Absolute mRNA quantification using the polymerase chain reaction (PCR). A novel approach by a PCR aided transcript titration assay (PATTY)," *Nucl. Acids Res.* 17(22):9437–9446 (1989).
Bergenhem, N. C. et al., "Mutation creates an open reading frame within the 5' untranslated region of macaque erythrocyte carbonic anhydrase (CA) I mRNA that suppresses CA I expression and supports the scanning model for translation," *Proc. Natl. Acad. Sci. USA* 89:8798–8802 (1992).
Beutler, E. et al., "Interference of Heparin with the Polymerase Chain Reaction," *BioTechniques* 9(2):166 (1990).
Bourinbaiar, A. S., "HIV and gag," *Nature* 349:111 (1991).
Bourinbaiar, A. S., "Weight of HIV," *Aids Res. Human Retrov.* 8(9):1545 (1992).
Brown, E. L. et al., "Chemical Synthesis and Cloning of a Tyrosine tRNA Gene," *Meth. Enzymol.* 68:109–151 (1979).
Butler, W. B., "Preparing Nuclei from Cells in Monolayer Cultures Suitable for Counting and for Following Synchronized Cells through the Cell Cycle," *Analytical Biochem.* 141:70–73 (1984).
Chelly, J. et al., "Quantitative estimation of minor mRNAs by cDNA–polymerase chain reaction: Application to dystrophin mRNA in cultured myogenic and brain cells," *Eur. J. Biochem* 187:691–698 (1990).
Chomczynski, P, and N. Sacchi, "Single Step Method of RNA Isolation by Acid Guanidium Thiocyanate–Phenol–Chloroform Extraction," *Analytical Biochem.* 162:156–159 (1987).
Clementi, M. et al., "Quantitative PCR and RT–PCR in Virology," *PCR Meth. Applic.* 2(3):191–196 (Feb. 1993).

(List continued on next page.)

Primary Examiner—Kenneth R. Horlick
Assistant Examiner—Jeffrey Siew
Attorney, Agent, or Firm—Sterne, Kessler, Goldstein & Fox, P.L.L.C.

[57] ABSTRACT

The invention relates generally to the quantitation of virus and viral nucleic acid. The invention relates to methods for quantitating an amount of virus present in a sample, comprising introducing into the sample a composition comprising a genetically tagged viral nucleic acid, isolating said wild type and said tagged nucleic acid, and quantitating said wild type and said tagged nucleic acid. The invention also relates to genetically tagged retroviral nucleic acid comprising a tag sequence, including insertions and deletions.

20 Claims, 6 Drawing Sheets

OTHER PUBLICATIONS

Coutlée, F. et al., "Discordance between Primer Pairs in the Polymerase Chain Reaction for Detection of Human Immunodeficiency Virus Type 1: A Role for Taq Polymerase Inhibitors," *J. Infec. Dis.* 164:817–818 (1991).

de Franchis, R. et al., "A potent inhibitor of Taq polymerase copurifies with human genomic DNA," *Nuc. Acids Res.* 16(21):10355 (1988).

Ferre, F., "Quantitative of Semi–Quantitative PCR: Reality Versus Myth," *PCR Meth. Applic.* 2:1–9 (1992).

Gilliand, G. et al., "Analysis of cytokine mRNA and DNA: Detection and quantitation by competitive polymerase chain reaction," *Proc. Natl. Acad. Sci USA* 87:2725–2729 (1990).

Green, M. et al, "Transcriptional Activation of Cloned Human β–Globin Genes by Viral Immediate–Early Gene Products," *Cell* 35:137–148 (1983).

Hämmerling, G. et al., "Production of Antibody–Producing Hybridomas i the Rodent Systems," In *Monoclonal Antibodies and T–Cell Hybridomas*, Elsevier, pp. 563–587 (1981).

Harada, S. et al., "Infection of HTLV–III/LAV in HTLV–I—Carrying Cells MT–2 and MT–4 and Application in a Plaque Assay," *Science* 229:563–566 (1985).

Holodniy, M. et al., "Inhibition of Human Immunodeficiency Virus Gene Amplification by Heparin," *J. Clin. Microbiol.* 29(4):676–679 (1991).

Jat, P. and P. Sharp, "Large T Antigens of Simian Virus 40 and Polyomavirus Efficiently Establish Primary Fibroblasts," *J. Virol.* 59(3):746–750 (1986).

Johnson, R. et al., "Autoradiography using storage phosphor technolgy," *Electrophoresis* 11:355–360 (1990).

Köhler, G. and C. Milstein, "Derivation of specific antibody–producing tissue culture and tumor lines by cell fusion," *Eur. J. Immunol.* 6:511–519 (1976).

Köhler, G. et al., "Fusion between immunoglobul in–secreting and nonsecreting myeloma cell lines," *Eur. J. Immunol.* 6:292–295 (1976).

Köhler, G. and C. Milstein, "Continuous cultures of fused cells secreting antibody of predefined specificity," *Nature* 256:495–497 (1975).

Meinkoth, J. and G. Wahl, "Hybridization of Nucleic Acids Immobilized on Solid Supports," *Analytical Biochem.* 138:267–284 (1984).

Melton, D. et al., "Efficient in vitro synthesis of biologically active RNA and RNA hybridization probes from plasmids containing a bacteriophage SP6 promter," *Nucl. Acids Res.* 12(18):7035–7056 (1984).

Menzo, S. et a., "Absolute Quantitation of Viremia in Human Immunodeficiency Virus Infection by Competitive Reverse transcription and Polymerase Chain Reaction," *J. Clin. Microbiol.* 30(7):1752–1757 (1992).

Mulllis, K. and F. Faloona, "Specific Synthesis of DNA in Virto via a Polymerase–Catalyzed Chain Reaction," *Meth. Enzymol.* 155:335–350 (1987).

Narang, S. et al., "Improved Phosphotriester Method for the Synthesis of Gene Fragments," *Meth. Enzymol.* 68:90–98 (1979).

Orkin, S. et al., "Base Substitution at Position —88 in a γ–Thalassemic Globin Gene," *J. Biol. Chem.* 259(14):8679–8681 (1984).

Piatak, M. et al., "Quantitative Competitive Polymerase Chain Reaction for Accurate Quantitation of HIV DNA and RNA Species," *BioTechniques* 14(1):70–80 (Jan. 1993).

Psallidopoulos, M. et al., "Integrated Proviral Human Immunodeficiency Virus Type 1 Is Present in CD4+ Peripheral Blood Lymphocytes in Healthy Seropositive Individuals," *J. Virol.* 63(11):4626–4631 (1989).

Sardelli, A., "Plateau Effect —Understanding PCR Limitations," *Amplifications: A Forum for PCR Users*(9):1 and 3–5 (Mar. 1993).

Siebert, P. and J. Larrick, "Competitive PCR," *Nature* 359:557–558 (1992).

Wang, A. et al., "Quantitation of mRNA by the polymerase chain reaction," *Proc. Natl. Acad. Sci. USA* 86:9717–9721 (1989).

INTERNALLY CONTROLLED VIRION NUCLEIC ACID AMPLIFICATION REACTION FOR QUANTITATION OF VIRION AND VIRION NUCLEIC ACID

This application is a continuation of Ser. No. 08/658,216, filed Jun. 4, 1996, now abandoned which is a continuation of Ser. No. 08/258,288 filed Oct. 4, 1994, now U.S. Pat. No. 5,814,442.

STATEMENT AS TO RIGHTS TO INVENTIONS MADE Under Federally-Sponsored Research and Development Government support under the National Institutes of Health NIAID grant number NO1-A1-05058. The Government has certain rights in the invention.

FIELD OF THE INVENTION

The invention relates generally to methods for quantitating virus following nucleic acid amplification. The invention also relates to genetically tagged retroviral nucleic acid capable of being distinguished from the wild type viral nucleic acid.

BACKGROUND OF THE INVENTION

Quantitative PCR has been used to measure the relative levels of RNA and DNA from a variety of different samples. It is possible, at times, to find a direct correlation between the amount of starting target material and the amount of PCR product (Mullis and Faloona, *Methods Enzymol.* 155:335–50 (1987); Ferre, F., *PCR Methods Applic.* 2:1–9 (1992); Sardelli, A. D., *Amplifications: A Forum for PCR Users* (9):1–5 (1993)). However, this is often not the case for clinical samples due to the presence of inhibitors of PCR in samples and differing efficiencies in sample recovery and kinetics of PCR (Holodniy et al., *J. Clin. Micro.* 29:676–679 (1991); Beutler et al., *BioTechniques* 9:166 (1990); Franchis et al., *Nucl. Acids Res.* 16:10355 (1988); Coutlée et al., *J. Infect. Dis.* 164:817–818 (1991)). The use of PCR as a quantitative assay often presents problems. For instance, small variations in amplification efficiency can change the yield of the product and make it difficult to accurately estimate the amount present in the starting material (Gilliland et al., *Proc. Natl. Acad. Sci. USA* 87:2725–2729 (1990)). To avoid these problems, several laboratories have described the use of internal standards in PCR (Gilliland et al., *Proc. Natl. Acad. Sci. USA* 87:2725–2729 (1990); Wang et al., *Proc. Natl. Acad. Sci. USA* 86:9717–9721 (1989); Becker-André et al., *Nucl. Acids Res.* 17:9437–9446 (1990); Chelly et al., *Eur. J. Biochem.* 187:691–698 (1990); Bergenhem et al., *Proc. Natl. Acad. Sci. USA* 89:8798–8802 (1992); Aoki-Sei et al., *AIDS Res. Human Retro.* 8:1263–1270 (1992); Siebert et al., *Nature* 359:557–558 (1992)). Generally, the internal standard DNA or RNA share the same primers as the target DNA or RNA, but will contain either a deletion or an insertion so that the products obtained from the standard and target can be distinguished.

A variation in the use of an internal control is the competitive PCR procedure (Gilliland et al., *Proc. Natl. Acad. Sci. USA* 87:2725–2729 (1990)). In this method, varying known amounts of the internal standards are added to equal aliquots of the sample containing the unknown target sequence. The internal standard and the target sequence compete equally for primer binding and amplification in the PCR. Variables such as the efficiency of amplification and the number of cycles will have the same effect on both templates. Equal amounts of products will be formed when the initial concentrations of the templates are equal. Experimentally, the ratio of products formed can be determined and the equivalence point can be calculated. This method has been successfully employed to quantify the amount of HIV-1 RNAs in clinical samples (Bagnarelli et al., *J. Med. Virol.* 34:89–95 (1991); Menzo et al., *J. Clin. Microbiol.* 30:1752–1757 (1992)). However, this method does not control the variations in RNA recovery from sample to sample. Similarly, viral DNA isolation is often incomplete and control of the amount of DNA would be of great use.

In the present invention, the inventors have developed a modified method in which an infectious tagged virus is used as the source of competitor nucleic acid. The tagged virus is a mutant or variant of the virus suspected of being in the sample. Different amounts of the tagged virus can be added to equal aliquots of the sample containing an unknown amount of virus, followed by nucleic acid extraction and amplification carried out in a manner that allows for relatively precise quantitation of the amount of viral nucleic acid present in the sample.

SUMMARY OF THE INVENTION

The inventors have developed an assay to measure the viral nucleic acid in any sample using a mutant (tagged) virus as an internal control. The mutant virus has a sequence tag in a region of the genome. To utilize this virus as an internal control, a dilution or dilutions of this virus are added to aliquots of samples to be measured, and nucleic acid is isolated, amplified, and quantitated.

Amplification is performed with primers selected to include the sequences capable of amplifying sequence containing the tag in the externally added virus. The amplification product from the control virus can be differentiated from the virus present in the sample. The amount of viral nucleic acid present in the sample is calculated after the amplified products are detected. Unlike other quantitative amplification assays, such as conventional PCR, this internally controlled virion amplification assay eliminates errors introduced by variable recovery during the viral nucleic acid purification step, therefore, enhancing the accuracy of the assay.

Accordingly, a preferred embodiment of the present invention is a method for quantitating the amount of virus present in a sample, the method comprising the steps of: introducing into said sample a composition comprising a virus containing a genetically tagged viral nucleic acid; co-isolating said wild type and said tagged nucleic acid from the sample; amplifying said wild type and said tagged nucleic acid from said sample; and quantitating said wild type and said tagged nucleic acid.

The invention further provides a genetically tagged retroviral nucleic acid comprising a tag sequence in a highly conserved region of said retroviral nucleic acid, wherein said tag occurs between the retroviral primer-binding and gag initiation sites.

BRIEF DESCRIPTION OF THE FIGURES

FIG. 2A–C depicts data of an estimation of the RNA isolated from the mutant virus VX-46. The amount of radioactivity present in bands corresponding to wild type and mutant PCR products were estimated by exposing it to a storage Phosphor screen and quantitated using a Molecular Dynamics PhosporImager (Johnston et al., *Electrophoresis* 11:355–360 (1990)). The ratio between the amount of radioactivity present in wild type (pA1) and mutant (VX-46) DNA bands was plotted against the amount of wild type DNA used in the PCR. The mutant viral RNA was isolated from virus containing 100 pg (FIG. 2A), 25 pg (FIG. 2B) and 500 fg (FIG. 2C) of p24 antigen respectively. The data derived from FIG. 1 is shown in Panel A. The RNA isolated from virus containing 25 pg (Panel B) and 500 fg (Panel C) of p24 were used to synthesize cDNA in a 40 $\mu$l reaction and 3 $\mu$l of cDNA were used in competitive PCR. Based on the method described by Menzo et al. (Menzo et al., *J. Clin. Microbiol.* 30:1752–1757 (1992)), it was calculated that 2 $\mu$l of cDNA in (Panel A) has 9500, 3 $\mu$l of cDNA in (Panel B) has 5200 and 3 $\mu$l of cDNA in (Panel C) has 120 copies respectively.

FIG. 3A–C depicts ICVPCR for the estimation of HIV-1 RNA in a human patient's plasma.

FIGS. 3A and 3B. To 100 $\mu$l aliquots of patient's plasma, different dilutions of mutant virus (VX-46) containing 0 (lane 1), 30 (lane 2), 3 (lane 3) 0.3 (lane 4) and 0.03 (lane 5) pg of p24 antigen were added. RNA isolation, cDNA synthesis and PCR were carried out as described in Materials and Methods. The size of DNA products from mutant (148) and wild type (123) are shown on the right. Panels A and B were plasma from two different human patients.

FIG. 3C. The radioactivity present in each band was quantitated using a Molecular Dynamics PhosporImager. The ratio between the radioactivity present in mutant and patient DNA bands was plotted against the amount of mutant viral RNA added to the patient's plasma during RNA isolation. The mutant viral RNA copy numbers were calculated using the average value (2900 copies of RNA per pg of p24 antigen) obtained with the data shown in FIG. 2. Patient-1 (Δ----- Δ) has 8,800 copies and the patient-2 (○----- ○) has 1600 copies of RNA in 100 $\mu$l of plasma.

FIGS. 4A & 4B depicts data demonstrating the reproducibility of ICVPCR

FIG. 4A. To 100 $\mu$l aliquots of patient's plasma, different dilutions of mutant virus (VX-46) containing 0 (lane 1), 24 (lanes 2 and 6), 2.4 (lane 3 and 7) 0.24 (lane 4 and 8) and 0.024 (lane 5 and 9) pg of p24 antigen were added. RNA isolation, cDNA synthesis, PCR and gel analysis for lanes 1 to 5 and 6 to 9 were carried out by two separate experiments on different days. The size of DNA products from mutant (148) and wild type (123) are shown on the right.

FIG. 4B. The radioactivity present in each band was quantitated and plotted as described in Materials and methods. The data for (Δ----- Δ) were from lanes 2 to 5 and the data for (○---- ○) were from the lanes 6 to 9.

DETAILED DESCRIPTION OF THE PREFERRED EMBODIMENTS

I. Introduction

The invention provides methods to measure the viral nucleic acid in a sample from individuals using a mutant (tagged) virus as an internal control. Preferred embodiments provide an infectious tagged virus. The mutant virus has a sequence tag in a conserved region of the genome. To utilize this virus as an internal control, a dilution or dilutions of this virus are added to aliquots of samples to be measured, nucleic acid is isolated and amplified with primers capable of amplifying sequence containing the tag in the externally added virus. The amplification product from the control virus can be differentiated from the virus present in the sample. The amount of viral nucleic acid present in the sample is calculated after the amplified products are detected.

"Amplification," as used herein, refers to any in vitro process for increasing the number of copies of a nucleotide sequence or sequences. Nucleic acid amplification results in the incorporation of nucleotides into DNA or RNA. As used herein, one amplification reaction may consist of many rounds of DNA replication. For example, one PCR reaction may consist of 30–100 "cycles" of denaturation or replication. Typical techniques for carrying out amplification include, but are not limited to PCR (see, for example, U.S. Pat. Nos. 4,683,195 and 4,683,202), LCR (Barany, *Proc. Natl. Acad. Sci. USA* 88:189–193 (1991), repair chain reaction (RCR) and 3SR (see, for example, European Patent Publication No. 373,960), including specific kinds of 3SR, such as, nucleic acid based amplification (NASBA), transcription mediated amplification (TMA) and strand displacement amplification (SDA).

The term "primer" refers generally to a nucleic acid molecule capable of hybridizing to the template nucleic acid and priming polymerization on the template. The term is to be construed to encompass, but not be limited to, deoxyribonucleic acid or derivatives thereof.

As used herein, the term "template" refers to a nucleic acid molecule that a nucleotide polymerase will use for the polymerization. The template molecule may be polymerized either partially or fully having either all of its nucleotide residues polymerization copied or having any number of its residues polymerization copied. In one preferred embodiment the nucleic acid template is comprised of ribonucleic acid and that the polymerase be reverse transcriptase. In another preferred embodiment the template be DNA and the polymerase is a DNA-directed-DNA-polymerase, such as Taq polymerase.

"Nucleotide," as used herein, is a term of art that refers to a base-sugar-phosphate combination. Nucleotides are the monomeric units of nucleic acid polymers, i.e., of DNA and RNA. The term includes ribonucleoside triphosphates, such as rATP, rCTP, rGTP, or rUTP, and deoxyribonucleotide triphosphates, such as dATP, dCTP, dGTP, or dTTP. A "nucleoside" is a base-sugar combination, i.e., a nucleotide lacking phosphate. It is recognized in the art that there is a certain interchangeability in the usage of the terms "nucleoside" and "nucleotide."

By "PCR"is meant herein the polymerase chain reaction (PCR) technique, disclosed by Mullis in the U.S. Pat. Nos. 4,683,195 (Mullis etal.) and 4,683,202, incorporated herein by reference. In the PCR technique, preferably short oligonucleotide primers are prepared which match opposite ends of a desired sequence. The sequence between the primers need not be known. A sample of DNA (or RNA) is extracted and denatured (preferably by heat). Then, oligonucleotide primers are added in molar excess, along with dNTPs and a polymerase (preferably Taq polymerase, which is stable to heat). The DNA is replicated, then again denatured. This results in two "long products," which begin with the respective primers, and the two original strands (per duplex DNA molecule). The reaction mixture is then returned to polymerizing conditions (e.g., by lowering the temperature, inactivating a denaturing agent, or adding more polymerase), and a second cycle initiated. The second cycle provides the two original strands, the two long products from cycle 1, two new long products (replicated from the original strands), and two "short products" replicated from the long products. The short products have the sequence of the target sequence (sense or antisense) with a primer at each end. On each additional cycle, an additional two long products are produced, and a number of short products equal to the number of long and short products remaining at the end of the previous cycle. Thus, the number of short products grows exponentially with each cycle. This amplification of a specific nucleic acid sequence allows the quantitation of extremely small quantities of DNA.

Figure 1:
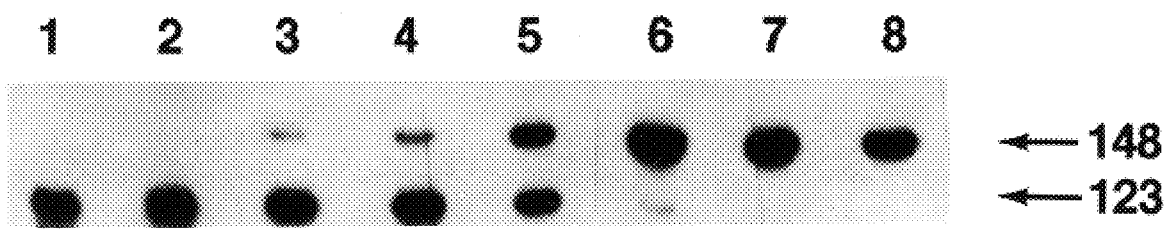
FIG. 1 depicts the use of cDNA synthesized from mutant virus (VX-46) RNA as competitor in PCR. RNA isolated from the mutant virus containing 100 pg of p24 antigen were used to synthesize cDNA in a 60 µl reaction. Two microliters of the cDNA were used in the PCR containing various amounts of competitor wild type DNA (pA1) containing HIVNL4.3 sequences from 501 to 1448. The PCR was carried out and the products were hybridized with a $^{32}$P-probe and autoradiographed as described in Materials and Methods. The copy numbers of competitor DNA present in the reactions were $10^6$ (lane 1), $5 \times 10^5$ (lane 2), $10^5$ (lane 3), $5 \times 10^4$ (lane 4) $10^4$ (lane 5), $10^3$ (lane 6) $10^2$ (lane 7) and 0 (lane 8). The sizes shown on the right were the PCR products in bp from mutant and wild type sequences respectively.

The term "3SR" as used herein refers to a method of target nucleic acid amplification also known as the "self-sustained sequence replication" system as described in European Patent Publication No. 373,960 (published Jun. 20, 1990).

The term "LCR" as used herein refers to a method of target nucleic acid amplification also known as the "ligase chain reaction" as described by Barany, *Proc. Natl. Acad. Sci. USA* 88:189–193 (1991).

The terms "tag" or "tagged" as used herein to describe a genetic sequence refer generally a nucleic acid sequence that is derived from a wild type virus or is synthesized from the sequence of a wild type virus and which differs from the sequence of the wild type virus nucleic acid by comprising a sequence insertion, deletion, or point mutation, or any combination of these mutations, such that the tagged nucleic acid can be differentiated from the wild type virus from which it is derived or a wild type virus of the same species. A tagged virus is a virus comprising a tagged nucleic acid sequence. The tag may in certain instances code for amino acid sequences that create a tagged protein as compared to a protein in the wild type virus.

Amplification in the methods of the invention can be performed using any of the amplification techniques known in the art, particularly those described and defined in the forgoing.

In preferred embodiments of this invention, the nucleic acid is amplified using PCR as described herein. Suitable PCR primers are prepared by means known to those of ordinary skill in the art, for example by cloning and restriction of appropriate sequences, or by direct chemical synthesis. For example, one may employ the phosphotriester method described by Narang et al., *Meth. Enzymol.* 68:90 (1979) and U.S. Pat. No. 4,356,270, incorporated herein by reference. Alternatively, one may use the phosphodiester method disclosed in Brown et al., *Meth. Enzymol.* 68:109 (1979), incorporated herein by reference. Other methods include the phosphoramidite method disclosed in Beaucage et at., *Tetrahedron Letts.* 22:1859–1862 (1981), and the solid support method in U.S. Pat. No. 4,458,066. The primers may also be labeled, if desired, by incorporating means detectable by spectroscopic, photochemical, biochemical, immunochemical, or chemical means. For example, the primer may include $^{32}P$, fluorescent dyes, electron-dense reagents, enzymes (as commonly used in ELISAs), biotin, or haptens or proteins for which antisera or monoclonal antibodies are available. The label should be selected to withstand denaturing conditions if it is to be attached directly to the primer.

When the nucleic acid strand to be amplified has been separated from contaminating material, it is ready to be used as a template for the synthesis of additional nucleic acid strands. This synthesis can be performed using any suitable method. The reaction is generally conducted in a buffered aqueous solution, preferably at a pH of 2–9, most preferably about 8. Preferably, a molar excess (for cloned nucleic acid, usually about 1000:1 primer/template, and for genomic or viral nucleic acid, usually about $10^8$:1 primer:template) of the two oligonucleotide primers is added to the buffer containing the separated template strands. It is understood, however, that the amount of complementary strand may not be known, so the amount of primer relative to the amount of complementary strand cannot be determined with certainty. A large molar excess is preferred to improve the efficiency of the process. These conditions are to be considered general guidelines for carrying out the reaction. Skilled artisan will understand how to carry out this reaction using a variety of buffers and conditions in view of the state of the art.

The deoxyribonucleoside triphosphates dATP, dCTP, dGTP and dTTP are also added to the synthesis mixture in adequate amounts and the resulting solution is heated to about 90–100° C. for about 1 to 10 minutes, preferably from 1 to 4 minutes. After heating, the solution is allowed to cool to room temperature, which is preferred for the primer hybridization. To the cooled mixture is added a polymerization agent, and the reaction is conducted under conditions known in the art. This synthesis reaction may occur at from room temperature up to a temperature above which the polymerization agent no longer functions efficiently. Thus, for example, if an *E. coli* DNA polymerase is used as the polymerizing agent, the maximum temperature is generally no greater than about 40° C. Most conveniently, the reaction using *E. coli* polymerase occurs at room temperature. Where greater stringency is desired, the reaction is performed using the thermostable enzyme Taq polymerase at elevated temperature.

The polymerization agent may be any compound or system which will function to accomplish the synthesis of primer extension products from nucleotide triphosphates, including enzymes. Suitable enzymes for this purpose include, for example, *E. coli* DNA polymerase I, Klenow fragment of *E. coli* DNA polymerase I, T4 DNA polymerase, and other available DNA polymerases, reverse transcriptase, and other enzymes, including heat-stable enzymes such as Taq polymerase, which will facilitate combination of the nucleotides in the proper manner to form the primer extension products which are complementary to each nucleic acid strand. Generally, the synthesis will be initiated at the 3' end of the primer and chain elongation of the newly synthesized strand will proceed in the 5' direction, until synthesis terminates, producing molecules of different lengths. There may be agents, however, which initiate synthesis at the 5' end and proceed in the other direction, using the same process as described above: use of such agents in the process of the invention is also to be considered within the scope of this invention.

The newly synthesized nucleic acid-complementary strand and the original nucleic acid strand form a double-stranded molecule which is used in the succeeding steps of the process. In the next step, the strands of the duplex molecule are separated using any of the procedures described above to provide single-stranded molecules.

New nucleic acid is synthesized on the single-stranded molecules. Additional polymerization agent, nucleotides and primers may be added if necessary for the reaction to proceed under the conditions prescribed above. Again, the synthesis will be initiated at one end of the oligonucleotide primers and will proceed along the single strands of the template to produce additional nucleic acid. After this step, half of the extension product will consist of the specific nucleic acid sequence bounded by the two primers.

The steps of strand separation and extension product synthesis can be repeated as often as needed to produce the desired quantity of the specific nucleic acid sequence. As will be described in further detail below, the amount of the specific nucleic acid sequence produced will accumulate in the exponential fashion.

If desired, one may amplify the target sequence in two stages, using nested primers. This variation may be used as a means for increasing the specificity of the reaction. The primer binding regions are selected so that the second set (arresting primers) bind to regions of the nucleic acid sequence between the primer binding regions for the first set (thus insuring that the second set binding regions will be amplified if present). The amplification process may be terminated at any time once a detectable quantity of polynucleotide has accumulated.

II. Methods for Quantitating Virus

The methods and tagged virus and viral nucleic acid of the invention are useful for the quantitation of viral nucleic acid and viral particles.

Accordingly, a preferred embodiment of the present invention is a method for quantitating the amount of virus present in a sample, the method comprising the steps of: introducing into said sample a composition comprising a virus containing a genetically tagged viral nucleic acid; co-isolating said wild type and said tagged nucleic acid from the sample; amplifying said wild type and said tagged nucleic acid from said sample; and quantitating said wild type and said tagged nucleic acid following nucleic acid amplification.

In an embodiment of the method for quantitating the amount of virus present in a sample, the sample is obtained from an individual suspected to be infected by a virus.

As used herein, the term "individual" refers generally to a single specimen or member of an organism-group or species. The term is to be construed to encompass, but not be limited to, mammals, birds, reptiles and amphibians, but is especially directed to humans.

As used herein, the terms "isolating" and "providing" generally refer to preparing a compound to be tested or analyzed in a manner suitable for the test or analysis, or preparing an extract containing a compound to analyzed or tested. The terms are intended to encompass crude cell lysates and extracts containing nucleic acid as well as substantially purified nucleic acid. The term "co-isolating" encompasses the meaning of "isolating" and also refers to the isolation of more than one compound from a sample substantially simultaneously, and particularly refers to the isolation of more than one nucleic acid.

The methods of the invention are generally applicable to the accurate quantitation of any virus. For the DNA viruses, the methods of the invention provide an internal control for the quantitation of viral DNA, some of which degrades or is otherwise lost during isolation or manipulation. The internal control allows the skilled artisans to make an accurate determination of the virus titer or DNA quantity in the sample or individual.

Similarly, for the RNA viruses, the methods of the invention provide an internal control for the quantitation of viral RNA. The lability and sensitivity of RNA to degradation due to, for example, the ubiquity of RNases is well known. The invention is particularly useful for the quantitation of viral RNA or viral titer. Methods directed to RNA virus quantitation are preferred in the invention.

Viral nucleic acids of the invention can be isolated using any of the many methods known in the art for isolation. For example, RNA may be isolated by any of the many techniques known and used in the art. See, for example Chomczynski et al., *Anal. Biochem.* 162:156 (1987). DNA can be isolated, for example, by phenol extraction and ethanol precipitation. Moreover, skilled artisans will be able to readily develop alternative techniques for synthesizing and amplifying cDNA based on the methods of the invention. DNA may be isolated by phenol extraction followed by ethanol precipitation.

It is preferred that the viral nucleic acid be isolated prior to amplification. Isolation can be achieved using any of the many nucleic acid purification methods known in the art. However, it is not essential that the nucleic acids be purified. Nucleic acids of the invention need only be provided in a form that is capable of being amplified. For example, amplification may be carried out in situ or may be carried out in an a crude cell or sample lysate. Skilled artisans will understand how to perform in situ PCR in cells suspected of being infected.

Tagging and preparation of viruses that are useful as internal controls, and application of these tagged viruses in the methods of the invention, has broad applicability to a wide range of viruses. For example, it is preferred in the methods of the invention that viruses are selected from the group consisting of: herpesviruses (i.e., herpes simplex virus 1 and 2, varicella-zoster virus, cytomegalovirus, Epstein-Barr virus), papovaviruses (i.e., papillomaviruses and polyomaviruses), enteroviruses, rotaviruses, Norwalk Group of viruses, coronaviruses, enteric adenovirus, astroviruses, small round viruses, picorna-parvovirus-like, mini-reovirus, influenza viruses, paramyxoviruses (i.e., parainfluenza virus, respiratory syncytial virus, and mumps virus), measles virus, subacute sclerosing panencephalitis (SSPE), rubella (German measles), arboviruses (i.e., members of the families of Toggaviridae and Bunyaviridae, as well as arboviruses that cause fevers, rash, arthralgia, arboviruses that cause encephalitis, and arboviruses that cause hemorrhagic fevers), rhabdoviruses, Marburg viruses, Ebola viruses, vesicular stomatitis virus, arenaviruses (i.e., Junin virus in Argentina, Machupo virus in Bolivia, and Lassa fever in West Africa), hepatitis viruses (i.e., hepatitis A, hepatitis B, hepatitis C, and hepatitis delta), reoviruses and rhinoviruses.

Skilled artisans will understand that the methods of the invention can be used with both RNA and DNA viruses, and that the conditions used in any particular embodiment may depend in part on the nature of the nucleic acid of the genome. For example, the nucleic acid from DNA viruses can be isolated and directly amplified according to the methods of the invention or any amplification method known in the art, such as PCR. Moreover, for example, it is preferred that RNA viruses are reverse transcribed prior to amplification of their genomic nucleic acid. In this way reverse transcribed DNA can serve as the template for the synthesis of amplification products using any of the amplification reactions known in the art, and particularly PCR. However, it will be clear to skilled artisans that the same methods may be used for RNA and DNA viruses. For instance, if the nucleic acid being amplified for the quantitation of virus is mRNA, then the same method can be used for all viruses which synthesize mRNA.

A. Retroviral and RNA Virus Quantitation Methods

The following are preferred embodiments of the invention for being generally methods of quantitating RNA virus nucleic acid and particles.

In one embodiment of the invention the wild type viral nucleic acid is RNA, particularly retroviral RNA.

In another embodiment the viral RNA of the invention is retroviral RNA derived from an animal naturally capable of being infected by a retrovirus.

It is contemplated that the retroviral nucleic acids useful in the methods and constructs of the invention include, but are not limited to those derived from retroviruses, such as of the genus Cisternavirus A; Oncovirus B, including mouse mammary tumor viruses (MMTV-S (Bittner's virus), MMTV-P (GR virus), MMTV-L); Oncovirus C, such as Rous sarcoma virus, Rous-associated virus, chicken sarcoma viruses, leukosis viruses, reticuloendotheliosis viruses, pheasant viruses, murine sarcoma viruses, murine leukosis virus G (Gross or AKR virus), murine leukosis viruses (MLV-F, MLV-M, MLV-R (Friend, Maloney, Rauscher viruses)), murine radiation leukemia virus, murine endogenous viruses, rat leukosis virus, feline leukosis viruses, feline sarcoma virus, feline endogenous virus (RD114), hamster leukosis virus (HLV), porcine leukosis virus, bovine leukosis virus, primate sarcoma viruses (woolly monkey, gibbon, ape), primate sarcoma-associated virus, primate endogenous viruses (baboon endogenous virus, stumptail monkey virus, MAC-1, owl monkey virus (OMC-1)); Oncovirus D, including reptilian viruses, such as the viper virus, and non-reptilian viruses such as Mason-Pfizer monkey virus (MPMV), langur virus, and squirrel monkey virus; Lentivirus E, including Visna virus of sheep and Maedi virus; and Spumavirus F, including foamy viruses of primates, cats, humans, and bovids.

It is preferred that the nucleic acids of the invention be derived from any of the human retroviruses, particularly the human T cell leukemia viruses and human immunodeficiency viruses, as well as from hepatitis viruses A, B, C and delta.

It is most preferred in the methods of the invention that the retroviral RNA is derived from a virus selected from the group consisting of HTLV-I, HTLV-2, HIV-1 and HIV-2.

Further virus nucleic acids of the invention include ones derived from: Caulimoviruses, avian myoblastosis virus, simian immunodeficiency viruses, feline immunodeficiency viruses, and equine infectious anemia viruses.

Such viral nucleic acids will be particularly useful with the methods of the invention in veterinary practice and human clinical practice.

The methods of the invention preferably have a step which uses a virion particle as an internal control.

Preferred methods are provided to measure the HIV-I RNA in a sample from a patient using an infectious mutant virus as an internal control. For example, in a preferred method a mutant virus, having an insert, deletion or point mutation in a conserved region (the "tagged region") of the viral genome is constructed. To utilize this virus as an internal control, it is preferred that different dilutions of this virus are added to aliquots of a sample to be measured. In these methods it is more preferred that the sample contain or be blood, plasma or serum. It is most preferred that the sample comprises plasma. RNA is isolated from the sample and reverse transcribed to cDNA. Amplification is performed with primers selected to include the sequences on either side of the tagged region contained in the externally added virus. The DNA product from the control virus having the tagged region has a different nucleotide composition than that from the virus present in the sample. The amount of viral RNA present in a sample is calculated after the amplified products are separated by gel electrophoresis. An advantage to this method is it eliminates errors introduced by variable recovery during the nucleic acid purification step, therefore, enhancing the accuracy of the assay.

B. Samples Suspected to Contain Virus

Samples of the invention include, but are not limited to, any tissue, cell or fluid obtained from an individual that can potentially contain virus or viral nucleic acid, such as, for example, blood, cerebrospinal fluid, saliva, lymphatic fluid, seminal fluid, vaginal fluid, serum, plasma, lymphoid or lymphocyte cells, especially B cells, T cells, monocytes, polymorphonuclear cells and macrophages, epithelial cell, especially nasopharyngeal and upper respiratory tract epithelium, labial epithelium, tumor cells, respiratory secretion, especially nasopharyngeal secretions, brain tissue, virus vesicle tissue, fluid and associated matter, wart tissue, fluid and associated matter, feces, urine, pleural and pericardial fluid, milk, salivary gland tissue, negri body fluid, cells and associated matter, and hepatic cells.

Samples of the invention can be derived from many sources. It is preferred that the sample used in the methods is obtained from a mammal, particularly a mammal that is capable of being naturally infected by a retrovirus.

It is more preferred that the sample is obtained from a mammal selected from the group consisting of: murids, leporids, equids, cervids, suids, ovids, bovids, felids, canids, mustelids, pongids and humans.

It is preferred in the methods that the amplification of said quantitating step comprises the step of performing polymerase chain reaction.

The quantitating step of the methods of the invention preferably utilize a polymerase chain reaction, particularly following a reverse transcription reaction step. Skilled artisans will be able to modify the reaction mixture and reagents to achieve useful reverse transcriptase activity using methods known in the art. Skilled artisans will be able to use any of the reverse transcription reaction mixes known in the art. See, for example, U.S. Pat. No. 5,183,949 in which a reaction mixture is disclosed in FIG. 1 in that patent.

It is preferred that the sample of the methods comprises blood and/or plasma.

Accordingly, a sample can be collected from individuals suspected of being infected by virus. It is most preferred that the sample comprises plasma that can be separated by centrifugation and stored until use. Aliquots of serial dilutions of a tagged virus can be added to the sample, and the mixed nucleic acid from tagged and wild type virus is co-isolated. It is preferred that the nucleic acid is precipitated by addition of an equal volume of alcohol and carrier tRNA. Nucleic acid is then recovered, preferably by centrifugation, washed and dissolved in buffer.

Samples used in the methods of the invention can be obtained by any of the various techniques known and employed in the art for obtaining tissues and fluids, including, but not being limited to, punch biopsying, swabbing, tissue aspiration, lavage, scraping and phlebotomization. It is contemplated by the invention that the tissue can be used directly for the extraction of protein or nucleic acid, or can be maintained in culture prior to such extractions. Cultured cells of the invention may comprise primary cells or immortalized cell lines. See, for example, Jat P. S. and Sharp, P. A., *J. Virol.* 59:746 (1986).

It may be advantageous to prepare cell lysates in the quantitating step in the methods of the invention. Cell lysates in the present invention can be simply prepared using, for example, chemical cytolysis, biological cytolysis and physical cytolysis, including maceration, trituration, alkaline lysis, detergent lysis, osmotic lysis, freeze-thaw lysis, and sonication.

If the sample in the methods comprises cells, the cells can be isolated in any of the many ways known in the art for isolating cells. Skilled artisans will recognize that cells may be obtained from an individual and used directly or maintained in culture prior to being used in the methods of the invention. Cells that are maintained in culture prior to being used in the methods may be maintained, for example, in standard tissue culture medium, such as MEM medium containing 10% fetal calf serum. Skilled artisans will recognize methods known in the art that are useful for stimulating the cells prior to use in the methods of the invention.

Cell numbers of isolated cells may be determined by methods known in the art, such as, for example, enumeration by culture counter or using a microscope and reticle (hemocytometer). See, for example, Butler, W. B., *Analytical Biochem.* 141:70–73 (1984).

C. Nucleic Acid Detection and Quantitation Methods

1. Amplification

Any method of nucleic acid amplification can be used in the amplification step in the methods of the invention. Preferred amplification reactions used in the methods of the invention include, for example, PCR (U.S. Pat. Nos. 4,683,195 and 4,683,202, 3SR (European Patent Application No. 373,960), LCR (Barany, *Proc. Natl. Acad. Sci. USA* 88:189–193 (1991), RCR and 3SR (see, for example, European Patent Publication No. 373,960), including specific kinds of 3SR, such as, NASBA, TMA and SDA.

It is preferred that the amplification step of the methods further comprises the step of performing a nucleic acid amplification chain reaction.

As used herein the term "nucleic acid amplification chain reaction" refers generally to any in vitro process for increasing the number of copies of a nucleotide sequence or sequences via a chain reaction, including, for example, PCR (see, for example, U.S. Pat. Nos. 4,683,195 and 4,683,202), LCR (Barany, *Proc. Natl. Acad. Sci. USA* 88:189–193 (1991), and RCR.

As discussed in the forgoing, the nature of the viral nucleic acid being obtained may dictate the preferred method by which it is obtained. In other words, amplification of DNA and RNA may require different techniques to be applied.

Reverse transcription can be used in the methods for the amplification of RNA virus genomic RNA or mRNA from any virus.

Amplification reactions can be used to quantitate the level of wild type virus or viral nucleic acid, quantitate the level of tagged virus or viral nucleic added to a sample, and to quantitate the level of tagged virus or viral nucleic added to a sample.

Amplification products can be analyzed and quantitated using techniques known in the art, such as gel electrophoresis analysis. In a preferred embodiment, PCR amplification product analysis is carried out as follows. A volume of PCR product is hybridized with a labelled oligonucleotide probe capable of hybridizing to the PCR product. The products are separated, preferably on a polyacrylamide gel and the probed products are detected, preferably by autoradiography (see, for example, Psallidopoulos et al., *J. Virol.* 63:4626–4631 (1989)). The amount of label present in each separated product is quantitated using techniques known in the art, preferably by using optical or radiometric scanning (see, for example, Johnston et al., *Electrophoresis* 11:355–360 (1990)). The amount of label present in each product sample is estimated and the ratio between the amount of label present in tagged and the wild type DNA bands is plotted against the input mutant viral RNA. Using this technique, the amount of viral RNA present in the samples is determined in the number of copies of RNAs per unit volume of sample obtained from the individual infected with virus.

It is preferred that a competitor internal control plasmid DNA is used in the reaction to estimate the amount of cDNA from the tagged virus following amplification. For example, to establish and standardize the assay, cDNA from tagged virus is PCR amplified in the presence of different amount of another control DNA. The different control DNA is selected so that the predicted DNA PCR products can be differentiated, preferably by size.

It is preferred that the quantitating step of the methods of the invention further comprises the step of co-isolating both of said wild type RNA and said tagged RNA. It is more preferred that the genetically tagged viral RNA comprises sequence derived from a retrovirus, particularly a retrovirus naturally capable of infecting an animal. It is most preferred that the retrovirus is a human retrovirus, particularly a retrovirus selected from the group consisting of HTLV-I, HTLV-II, HIV-1 and HIV-2.

Based on the approximate mass of the viral particle, which is known in the art or can be determined using methods known in the art (Bourinbaiar, A. S., *Nature* 349:111 (1991); Bourinbaiar, A. S., *Weight of HIV AIDS Res. Human Retrov.* 8:1545 (1992)), such as quantitative centrifugation, the quantity of virus and viral nucleic acid in any sample or preparation can be determined. Moreover, the copy numbers of viral nucleic acids can also be determined.

It would be understood by skilled artisans that detection and quantitation of polymers synthesized by amplification can be enhanced by labeling nucleotide monomers that will be incorporated into the polymerization products. One skilled in the art will immediately recognize that these labeling materials will also be useful to label the polymerization products following their synthesis and any compounds that are useful for the detection and quantitation of the polymerization products, such as, for example, hybridization probes.

It is preferred that the quantitating step of the methods further comprises introducing a hybridization probe into said wild type and said tagged DNA products of the polymerase chain reaction.

It is preferred in the methods that the oligonucleotide is a labelled hybridization probe.

It is preferred that in the methods of the invention that the quantitating step further comprises the step of separating the DNA polymerase chain reaction products. It more preferred that the separating step further comprises electrophoresis of the DNA products.

A preferred embodiment of the amplifying step of the above genetic methods further comprises the steps of: isolating RNA from the sample; contacting the RNA with at least one primer capable of priming cDNA synthesis; synthesizing first strand cDNA from the primers; contacting the cDNA with at least one primer capable of priming extension product synthesis; synthesizing primer extension products from the primers; and, amplifying the extension products using polymerase chain reaction to yield amplified nucleic acid.

Skilled artisans will be readily able to make primers useful for amplification, such as PCR primers. Certain primers can be obtained commercially or can be synthesized with a DNA synthesizer, such as, for example, an Applied Biosystems Inc DNA synthesizer (Foster City, Calif.).

Skilled artisans will readily recognize techniques by which levels of nucleic acid amplification can be detected, determined or quantitated such as, for example, by measurement of labeled nucleotides incorporated in the nucleic acid polymerized, measuring the number of certain residues in the nucleic acid polymerized or spectrographically measuring the absorptivity of the nucleic acid polymerized. Skilled artisans will also recognize numerous hybridization techniques whereby the amplification and polymerization can be detected, determined or quantitated, such as, for example, by chromatographic separation of polymerized products followed by hybridization with a labeled nucleic acid (See, for example, Haymes, et al. (in: Nucleic Acid Hybridization, A Practical Approach) IRL Press, Washington, D.C. (1985)). Another technique that may be employed to determine the level of amplification and polymerization is by labelling the primer nucleic acid and detecting a shift in the level of incorporated label to unincorporated label over time.

It will be understood by skilled artisans that the quantitation step or steps of the invention can be enhanced by labeling the detection or quantitation means. For example, detection and quantitation of polymers synthesized by amplification can be enhanced by labeling nucleotide monomers that will be incorporated into the amplification products. One skilled in the art will immediately recognize that labeling materials will also be useful to label the amplification products following their synthesis. Skilled artisans will know which compounds are useful for the detection and quantitation of amplification products, such as, for example, hybridization probes. Label will also be useful to enhance the detection and quantitation of an antibody used in the methods of the invention. Labels useful in the methods of the present invention include, but are not limited to, fluorescers, ligands, chromophores, chromogens, luminescers, including chemoluminescers and bioluminescers, and radionuclides. Skilled artisans will be able to select an appropriate label for any given means of detection, such means including for example, nucleotide monomers, oligonucleotides, antibodies, lectins, streptavidin-biotin, oligonucleotide intercalating agents and peptides, such as those useful for nucleic acid binding. Skilled artisans will be able to use such means of detection using techniques known in the art. See, for example, Sambrook (Sambrook et al., *Molecular Cloning—A Laboratory Manual* (2d ed.), Cold Spring Harbor Labs, Cold Spring Harbor, N.Y. (1989)).

Different concentrations or titers of viral nucleic acids or particles can be used in order to generate standard curves to which the wild type particle or nucleic acid quantities can be prepared. See, for example, Stryer, L. *Biochemistry,* 2nd Edition, W. H. Freeman and Co., San Francisco, Calif. (1981) for a general discussion of enzyme kinetics and inhibition; Remington's Pharmaceutical Sciences, 18 Edition, Mack Publishing Co., Easton, Pa. (1990) for a general discussion of displaying graphical data. Skilled artisans will be easily able to determine the quantity of viral particles per unit volume of the sample obtained from the individual. This will allow the wild type viral titer to be determined. In a clinical setting, knowledge of the viral titer is valuable information upon which to base the efficacy of treatment and the health of the individual. For example, the methods of the present invention will provide to the numerous individuals suffering from HIV infection, an important method for determining the efficacy of their therapies and the course of their infection. The methods provide a convenient way to accurately quantify the viral burden in an individual.

2. Hybridization

Nucleic acid of the invention can also be quantitated using hybridization techniques known in the art. Using these methods tagged nucleic acid molecules can be readily differentiated from wild type nucleic acid molecules. The nucleic acids of the present invention can be quantitated using hybridization techniques, such as for example, Northern and Southern blotting and RNase protection assays. For examples of nucleic acid hybridization techniques, see Meinkoth et al., *Anal. Biochem.* 138:267–284 (1984); Haymes, et al. (In: Nucleic Acid Hybridization, A Practical Approach. IRL Press, Washington, D.C. (1985), Melton, et al., *Nucl. Acids Res.* 12:7035–7056 (1984) and Sambrook, et al., *Molecular Cloning—A Laboratory Manual,* (Second Edition), Cold Spring Harbor Labs, Cold Springs Harbor, N.Y. (1989).

3. Antibody Techniques

Sequence tags present within open reading frames will be transcribed in viral RNAs, which can be translated so that the modified peptide produced can be detected and quantitated using an antibody. Certain of the tagged molecules will have novel epitopes engineered into them so that commercially available antibodies may be used for detection and quantitation. For example, the coding sequence for a heterologous epitope known to be recognized by a certain antibody can be fused to the coding sequence for a viral protein. In this way the tagged protein can be detected and quantitated. Using a second antibody specific for a viral epitope that is disturbed by the inserted tag, the skilled artisan can determine the level of wild type viral protein. Another example of an antibody quantitation method relies on the difference in molecular weight between the tagged protein and the wild type protein. Western blotting and immunoprecipitation are convenient for quantitating these two proteins and measuring their levels. These translation/antibody detection techniques will allow the skilled artisan to determine the level of in vitro synthesized wild type and tagged protein.

In vitro translation may be carried out using any of the methods known in the art, such as reticulocyte lysate translation.

The term "antibody", as used herein, refers to both monoclonal antibodies which are a substantially homogenous population and to polyclonal antibodies which are heterogenous populations. Antibodies may be from any immunoglobulin class, including IgG, IgM, IgE, IgA, IgD and any subclass thereof. The term "antibody", as used herein, is also meant to include both natural intact molecules and fragments thereof, such as, for example, Fab and F(ab')$_2$, which are capable of binding antigen or hapten, as well as fusion constructs capable of binding antigen or hapten comprising immunoglobulin fragments and fragments of other molecules. The term "antibody" is also to be construed to include humanized antibodies of various other species as well as immunoglobulins or fusions therefrom expressed in a prokaryotic cell.

Both monoclonal and polyclonal antibodies to wild type and tagged protein will be made according to methods well known in the art. See, for example, Ausubel et al., *Current Protocols in Molecular Biology,* published by Current Protocols, pp. 11.4.2–11.13.4 (1993). Hybridomas may be created using the cells of the present invention for the production of monoclonal antibodies. See, for example, Kohler et al., *Eur. J. Immuno.* 6:292 (1976). Antibodies may be generated against wild type and tagged proteins. Moreover, antibodies to wild type protein can be isolated from cells and tissues where they naturally occur.

It is contemplated by the present invention that substantially purified wild type and tagged protein will be useful in immunoassays. One skilled in the art can readily use substantially purified protein of the invention as the starting point to develop immunoassays using methods known in the art, such as, for example, radioimmunoassays, sandwich assays and immunodiffusion assays. See, for example, Kohler et al., *Nature* 256:495 (1975); Kohler et al., *Eur. J. Immunol.* 6:511 (1976); Kohler et al., *Eur. J. Immunol.* 6:292 (1976); Hammerling et al., *In Monoclonal Antibodies and T-Cell Hybridomas,* pp. 563–681, Elsevier, N (1981); Sambrook et al., *Molecular Cloning—A Laboratory Manual,* (Second Edition), Cold Spring Harbor Labs, Cold Spring Harbor, N.Y. (1989), especially Chapter 18 which outlines methods useful with substantially purified protein or antibodies raised to substantially purified protein. One method commonly known in the art is to make polyclonal or monoclonal antibodies to substantially purified proteins. See, for example, Harlowe, E. and Lane, D., *Antibodies a Laboratory Manual,* Cold Spring Harbor Laboratories, 1988.

4. Restriction Analysis

In an embodiment of the invention, the tagged nucleic acid can be distinguished from the wild type nucleic acid by restriction analysis. General approaches to restriction analysis include a method whereby the wild type virus contains a restriction site or sites which the tagged virus does not contain. Alternatively, the tagged virus can contain a restriction site or sites which the wild type virus does not contain. Novel sites can be engineered into the tag sequence using methods well known by skilled artisans (see, for example, Sambrook et al., *Molecular Cloning—A Laboratory Manual* (2d ed.), Cold Spring Harbor Labs, Cold Spring Harbor, N.Y. (1989) and Rodriguez et al., *Recombinant DNA Techniques: An Introduction,* The Benjamin/Cummings Publishing Co., Ontario (1983)). Following amplification, the novel site or sites can be digested with restriction endonuclease using techniques known in the art (see, for example, Sambrook et al., *Molecular Cloning—A Laboratory Manual* (2d ed.), Cold Spring Harbor Labs, Cold Spring Harbor, N.Y. (1989) and Rodriguez et al., *Recombinant DNA Techniques: An Introduction,* The Benjamin/Cummings Publishing Co., Ontario (1983)). Following digestion, the nucleic acid fragments can be separated, such as by, for example, gel electrophoresis, and the amounts of amplified nucleic in each band can be quantitated. It will be a simple matter to distinguish between the tagged and wild type viral nucleic acid, since the number and/or size of the products from the nucleic acids will be different.

A novel restriction site can be constructed in the tagged virus using insertion of a linker containing the site, point mutation to construct a site or deletion to join two regions an create a site. Moreover, the skilled artisan can select restriction sites to delete. This will also create a tagged virus having a different restriction pattern and restriction map to enable the skilled artisan to distinguish the tagged nucleic acid from the wild type nucleic acid.

As used herein the term "novel site" refers to a site which does not occur in the wild type viral genome at the position of the engineered site. However, the restriction site may exist somewhere else in the wild type viral genome.

In a preferred embodiment a infrequently occurring restriction site is constructed in the sequence tag. It is more preferred that the infrequently occurring restriction site is present only once in the tagged nucleic acid and is not present in the wild type virus. These constructs will yield a two band restriction pattern for the tagged virus and a single, larger band for the wild type virus.

III. Genetically Tagged Viral Nucleic Acids and Viral Particles

As used herein, the term "substantially pure" or "substantially purified" is meant to describe a compound which is substantially free of any compound associated with the compound in its natural state. For example, a protein which is substantially free from other proteins, nucleic acids, lipids and carbohydrates is considered to be substantially pure or purified. The term is further mean to describe a compound which is homogenous by one or more criteria of purity or homogeneity used by those of skill in the art. The terms "substantially pure" or "substantially purified" as use herein are not meant to exclude artificial, synthetic, or semi-synthetic mixtures or hybrids.

The invention also provides a genetically tagged retroviral nucleic acid comprising a tag sequence in a highly conserved region of said retroviral nucleic acid, for example, wherein said tag occurs between the retroviral primer-binding and gag initiation sites. For example, it is more preferred that a tag is constructed in a well conserved region between the primer binding and gag initiation sites of retroviruses (Myers et al., *Human Retroviruses and AIDS: A Compilation and Analysis of Nucleic Acid and Amino Acid Sequences,* Los Alamos National Laboratory, Los Alamos, N. Mex. (1992)). It is most preferred that the tag comprises an inserted sequence, particularly consisting essentially of the sequence: (SEQ ID NO:5) AGACATCTA-GACGCGTCTAGACGCG.

Tagged viral nucleic acids can be constructed using standard procedures as described in Sambrook et al. (Sambrook et al., *Molecular Cloning: A Laboratory Manual,* 2nd ed., Cold Spring Harbor laboratory, Cold Spring Harbor, N.Y. (1989)). For instance, the tagged region can be inserted or deleted from a DNA copy of a DNA or RNA virus and these DNA constructs can be substantially purified. These DNA constructs can also be transfected into host cell lines so that viral particles can be produced.

It is also preferred that the tag comprises fused nucleic acid said fused junction being defined by a deletion mutation of a wild type sequence.

If the tag is an insertion, it is preferred that the tag sequence is of a sufficient length that the wild type and mutant viral DNAs can be separated and identified after amplification. It is most preferred that an insert tag be between about 5 and 50 nucleotides in length. The sequence tag can be any number of nucleotides in length as long as the tag will not interfere with virus growth. Virus growth can be easily monitored using techniques known in the art and taught in the invention.

It is preferred that the retroviral RNA is derived from a retrovirus capable of naturally infecting an animal.

It is more preferred that the retroviral RNA is derived from human retroviral RNA selected from the group consisting of HTLV-I, HTLV-II, HIV-1 and HIV-2.

Viral particles can be prepared following the construction of the tagged virus. Viral DNA constructs can be transfected into cells and these cells can be culture to obtain viral particles. These viral particles can be isolated or used to infect another cell type so that more virus can be grown up. Skilled artisans will know methods for transfection of these viral constructs, such as, for example, calcium phosphate precipitation method (Sambrook et al., *Molecular Cloning: A Laboratory Manual,* 2nd ed., Cold Spring Harbor laboratory, Cold Spring Harbor, N.Y. (1989)).

Transfected cells can be maintained using methods well known in the art for mammalian cell culture, such as maintenance on MEM medium containing 10% fetal calf serum, or in RPMI 1640 medium containing 10% fetal calf serum (Harada et al., *Science* 229:563–566 (1985)).

For the transfection of HIV DNA constructs it is preferred that 293 cells or other suitable cell types are used, followed by reinfection of MT-2 cells. It is preferred that after transfection, the culture fluid is isolated and used to infect cells capable of being infected with virus. Upon establishment of the infected cells, it is preferred that cell-free virus was harvested, aliquotted and stored for use in the methods of the invention. It is also preferred that each aliquot is used only once in any one assay. The amount of virus in the culture supernatant can be estimated by any of the many techniques known in the art for quantitating virus titer. For example, HIV-1 titer can be determined by a p24 antigen ELISA assay using Coulter Corp (Hialeah, Fla.) reagents following the manufacturer's recommended protocol.

The invention also provides a virion particle comprising the genetically tagged viral nucleic acids of the invention.

IV. Kits for Quantitating Virus

It is preferred that the kits of the invention be hand-held and constructed of durable materials and comprising transparent compounds and reaction chambers so that reaction results can be readily determined by viewing the kit device. It is more preferred that the kit device comprise a reaction vessel useful to perform a reaction using a sample and reagents and reverse transcriptase capable of polymerizing DNA by reverse transcription. It is more preferred that the reaction vessel be enclosed so that once the reaction has begun substantially none of the compounds in the reaction can escape from the kit device.

It is preferred that the kits comprise a convenient plastic container for holding the various components. It is more preferred that the kits comprise a self-contained hand-held assay device whereby samples can be introduced, tested, results can be obtained, and the contaminated kit device can then be safely discarded. Those skilled in the art will recognize proper storage and stabilizing buffers for the reagents in the kits.

One skilled in the art could readily adapt the kits of the present invention to methods devised using methods of the present invention as a starting point.

Having now generally described this invention the same will be better understood by reference to certain specific examples which are included for the purposes of illustration and are not intended to limit it unless otherwise specified.

EXAMPLES

SUMMARY

The inventors have developed an assay to measure the HIV-I RNA in patients' plasma or sera using an infectious mutant virus as an internal control. The mutant virus, VX-46, has a 25 bp insert in a conserved region between the primer binding and major splice donor sites. To utilize this virus as an internal control, different dilutions of this virus were added to aliquot of plasma sample to be measured, RNA was isolated and reverse transcribed to cDNA. PCR was performed with primers selected to include the sequences on either side of the insert contained in the externally added virus. The DNA product from the control virus is 25 bp longer than that from the virus present in plasma. The amount of viral RNA present in a plasma sample is calculated after the PCR amplified products are separated by gel electrophoresis. Unlike other quantitative PCR assays, this internally controlled virion PCR (ICVPCR) assay eliminates errors introduced by variable recovery during the RNA purification step, therefore, enhancing the accuracy of the assay.

Materials and Methods

Cells.

293 cells were obtained from ATCC and maintained in MEM medium containing 10% fetal calf serum. MT-2 cells were obtained from Dr. D. Richman through the NIAID AIDS research program and were maintained in RPMI 1640 medium containing 10% fetal calf serum (Harada et al., *Science* 229:563–566 (1985)).

Generation of Mutant HIV-1 Virus. A well conserved region between the primer binding and gag initiation sites of HIV-1 was chosen for insertion (Myers et al., *Human Retroviruses and AIDS: A Compilation and Analysis of Nucleic Acid and Amino Acid Sequences,* Los Alamos National Laboratory, Los Alamos, N. Mex. (1992)). The plasmid pNL4.3, an infectious molecular clone of HIV-1 obtained from Dr. M. Martin was used as the starting material (Adachi et al., *J. Virol.* 59:284–291 (1986)). A mutant (VX-46) with the insert 5' (SEQ ID NO: 5) AGA-CATCTAGACGCGTCTAGACGCG 3' at nucleotide position 715 of pNL4.3 was generated using standard procedures as described in Sambrook et al. (Sambrook et al., *Molecular Cloning: A Laboratory Manual,* 2nd ed., Cold Spring Harbor laboratory, Cold Spring Harbor, N.Y. (1989)). The HIV-1 nucleotide numbering used is according to HIVNL4.3; Genbank accession number M19921. The VX-46 DNA was transfected into 293 cells by the calcium phosphate precipitation method (Sambrook et al., *Molecular Cloning: A Laboratory Manual,* 2nd ed., Cold Spring Harbor laboratory, Cold Spring Harbor, N.Y. (1989)). Forty eight hours after transfection, the culture fluid was taken and used to infect MT-2 cells. The mutant virus grew with similar kinetics as that of wild type virus. Cell free virus was harvested, aliquotted and stored at −70° C. Each aliquot was used once in ICVPCR experiments. The amount of virus in the culture supernatant was estimated by p24 antigen ELISA assay using Coulter Corp (Hialeah, Fla.) reagents following the manufacturer's recommended protocol.

PCR Primers

The ICVPCR primers described in Table 1 were synthesized with an Applied Biosystems Inc DNA synthesizer (Foster City, Calif.).

RNA Isolation and cDNA Synthesis

After informed consent had been obtained, whole blood samples were collected from HIV-1 seropositive patients in the presence of acid-citratedextrose as an anticoagulant. The plasma was separated by centrifugation and stored at −70° C. until use. Aliquots (100 μl) of serial dilutions of the mutant virus, VX46, were added to 100 μl of patient's plasma and RNA was extracted with 4.0 M guanidinium thiocyanate and phenol in the presence of 180 mM sodium acetate as described earlier (Chomczynski and Sacchi, *Anal. Biochem.* 162:156–159 (1987)). The RNA was precipitated by addition of an equal volume of isopropanol and 10 μg of carrier tRNA (Sigma Chemical Co).

RNA was recovered by centrifugation, washed with cold 70% ethanol and dissolved in 8.0 μl of DNAse buffer containing 50 mM Tris, pH 8.0, 5 mM $MgCl_2$ and 10 units of RNAse free DNAse (Boehringer Mannheim Biochemicals) and incubated at 25° C. for 30 min. The DNAse was inactivated at 80° C. for 10 min and the RNA was used for cDNA synthesis using a cDNA cycle kit obtained from Invitrogen Corporation (San Diego, Calif.). Briefly, 2 μl of 100 mM methyl mercuric hydroxide was added to 8 μl of RNA and after 5 min incubation at room temperature, 2.5 VI of 0.7 M β-mercaptoethanol was added and the reaction was kept on ice. To this was added 4.0 μl of 5X RT buffer (0.5 M Tris, pH 8.3, 0.2 M KCl and 50 mM $MgCl_2$), 1.0 μl of RNAse inhibitor, 1.0 μl of 25 mM of dNTPs, 1.0 μl of primer ICVPCR-9 (40 pmoles) and 0.5 μl of AMV reverse transcriptase (5 units) and it was incubated at 42° C. for one hour. Then the reaction was heated to 95° C. for 3 min and cooled on ice for 2 min and 5 more units of reverse transcriptase were added and the incubation was continued for another hour at 42° C. Finally, the reaction was heated to 95° C. for 3 min and the cDNA was either used in the PCR or stored at −20° C.

PCR

Five microliters of cDNA were used in a reaction containing 10 mM Tris-HCl, pH 8.3, 50 mM KCl, 1.5 mM $MgCl_2$, 0.001% gelatin, 0.2 mM dNTPs, 25 picomoles of primers ICVPCR-16 and 17 (Table 1) and 2.5 units of Taq DNA polymerase (Perkin-Elmer Cetus) in a final volume of 50 μl. The samples were amplified in a Perkin-Elmer Cetus thermocycler (9600) with the following PCR cycle program: one cycle: 94° C. for 60 sec, 55° C. for 10 sec and 72° C. for 30 sec; 30 cycles: 94° C. for 15 sec, 55° C. for 30 sec and 72° C. for 60 sec and a final incubation at 72° C. for 10 min. The samples were then stored at 4° C. until analysis. The competitor plasmid (pA1) DNA used to estimate the amount of cDNA from VX-46 virus contained pNL4.3 nucleotide sequences from 501 to 1448.

Analysis of the PCR Product

Fifteen microliters of PCR product were hybridized with 5'-$^{32}$P labelled oligonucleotide ICVPCR-18 (Table 1) and separated in a 10% polyacrylamide gel and autoradiographed as described earlier (Psallidopoulos et al., *J. Virol.* 63:4626–4631 (1989)). The amount of radioactivity present in each band was quantitated using either the Molecular Dynamics PhosporImager (Sunnyvale, Calif.) or Fuji Medical Systems BAS1000 (Stamford, Conn.) by exposing the gel to a storage phosphor screen as described by Johnston et al. (Johnston et al., *Electrophoresis* 11:355–360 (1990)).

Results and Discussion

Estimation of RNA Present in a VX46 Virus Preparation

Figure 2C:
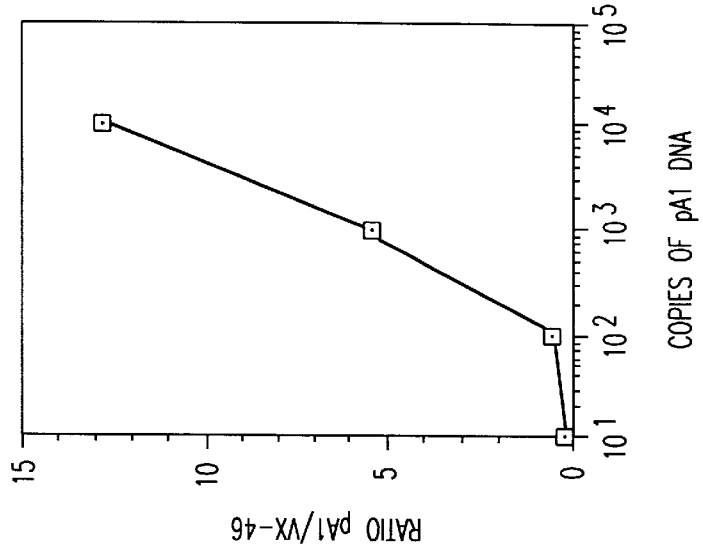
Figure 2B:
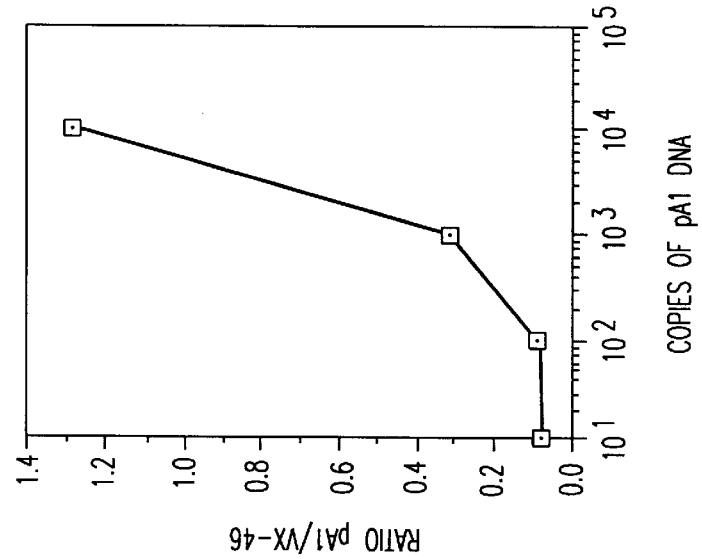
Figure 2A:
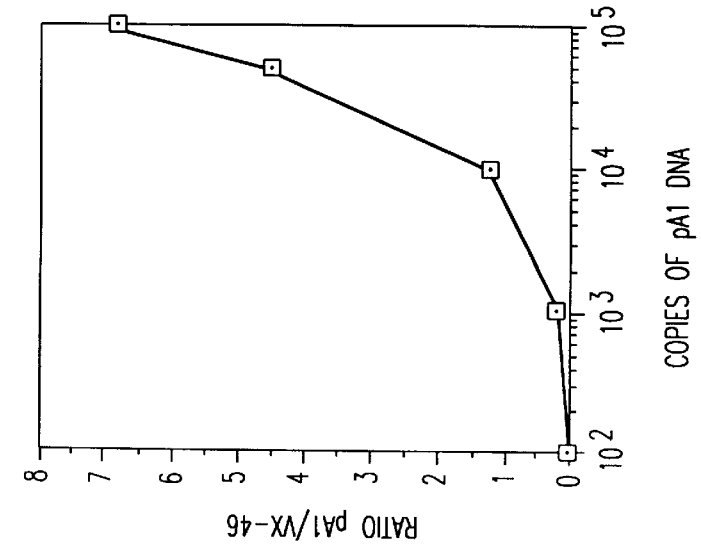

RNA was isolated from aliquots of VX-46 virus containing 100 pg, 25 pg or 500 fg of p24 antigen and cDNA was synthesized using standard conditions. To establish and standardize the assay, cDNA from VX-46 virus was PCR amplified in the presence of different amount of plasmid DNA (pA1) containing pNL4.3 nucleotide sequences from 501 to 1448. As shown in FIG. 1 the primers selected gave the predicted 123 bp and a 148 bp DNA PCR products from the wild type and mutant viral sequences respectively. In some experiments additional minor bands were seen. Most likely these are heteroduplexes formed between the two expected bands. Also the unused excess primer from the cDNA synthesis step can participate in the PCR react-ion and generate a longer product (seen in FIGS. 3 and 4). These bands do not interfere with accurate quantitation because the quantitation by this method is based on relative levels of bands from target and competitive templates and not on the absolute amounts (Piatak et al., *BioTechniques* 14:70–80 (1993)). The amounts of radioactivity in the specific bands were determined as described in Materials and Methods. The ratios between the amounts of radioactivity present in wild type and mutant DNA bands were plotted as described earlier (Bagnarelli et al., *J. Med. Virol.* 34:89–95 (1991)). Based on these data (FIG. 2), it was calculated that 285000, 69300 and 1600 copies of RNA were isolated from virus containing 100 pg, 25 pg and 500 fg of p24 antigen respectively.

Based on the mass of an HIV-I particle, a virus preparation with 100 pg of p24 would be calculated to contain one million HIV particles (Bourinbaiar, A. S., *Nature* 349:111 (1991); Bourinbaiar, A. S., *Weight of HIV AIDS Res. Human Retrov.* 8:1545 (1992)), or two million copies of RNA. Thus, the copy numbers determined in our experiment represent approximately 15% of the theoretical value. This reflects loss of RNA during extraction and lower than the theoretical yields in the preparation of cDNA. However the quantitation by competitive PCR relies on the relative levels of wild type and mutant templates, rather than the absolute amount. Therefore, once the determination of the amount of RNA in a mutant virus preparation is made, the recovery of RNA in each ICVPCR experiment does not affect the outcome of the results.

ICVPCR to Determine the Level of HIV-1 RNA in Plasma

Figure 3A:
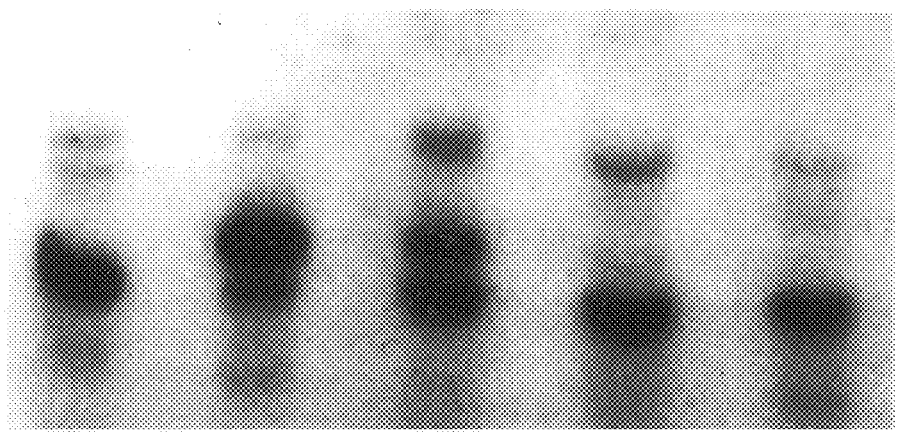
Figure 3B:
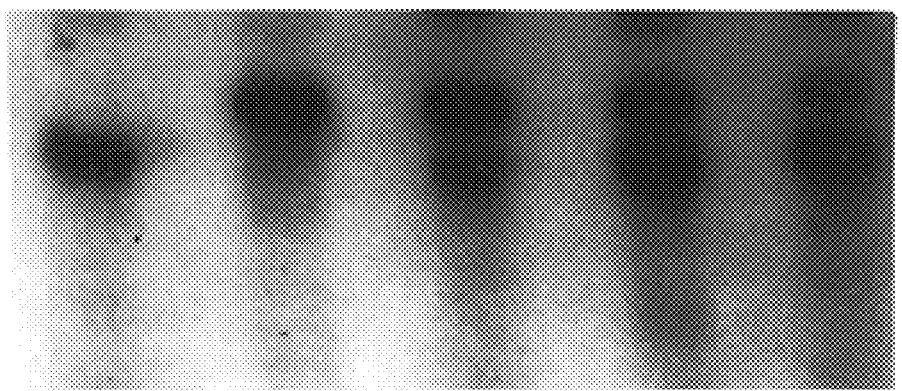
Figure 3C:
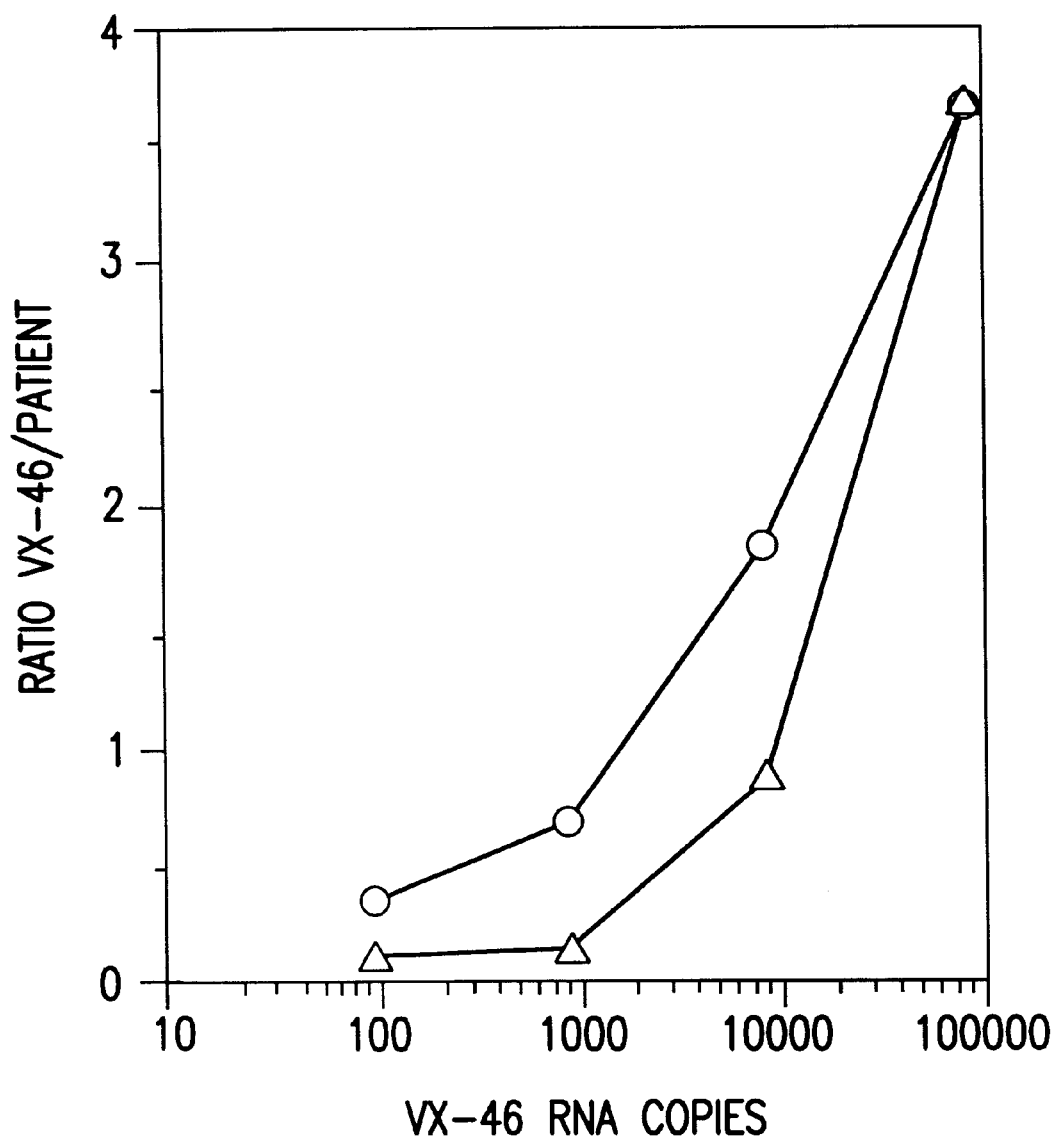
Figure 4A:
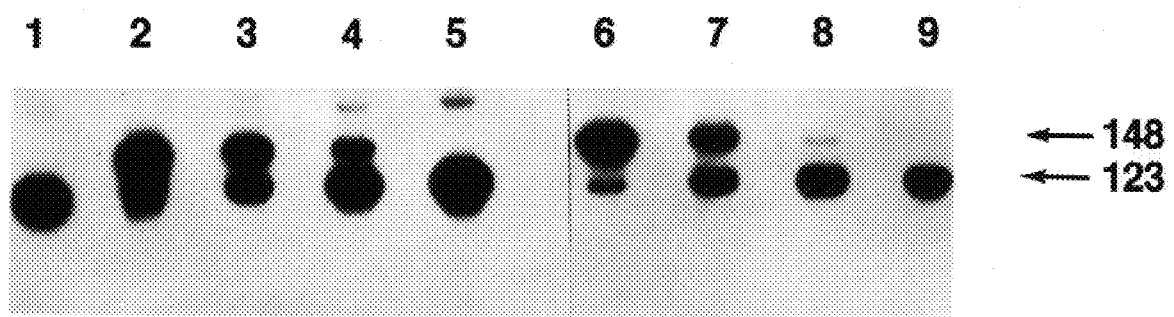
Figure 4B:
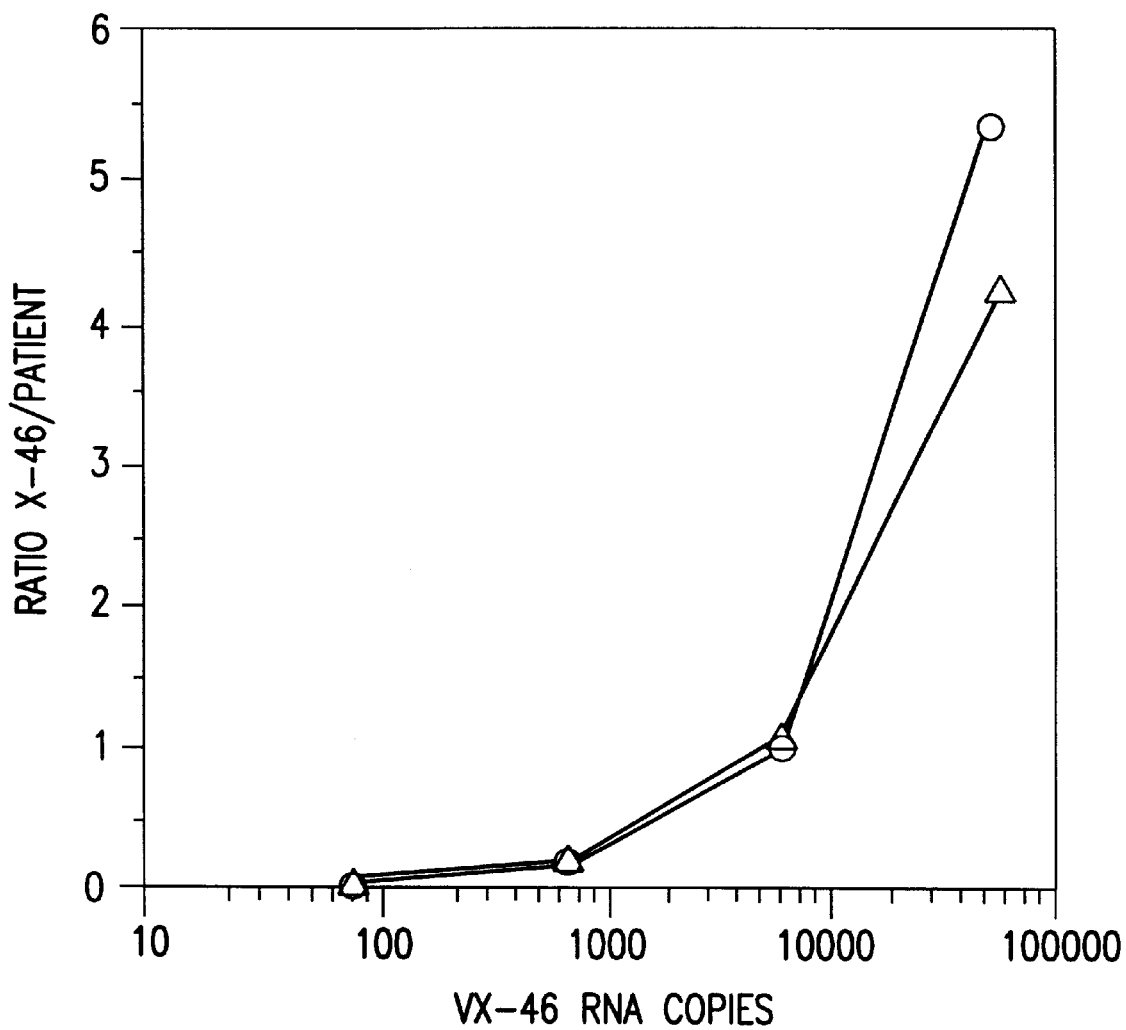

Using this standardized VX-46 virus as the competitor during the RNA isolation, the amount of HIV-I viral RNA in patient's plasma was estimated. The results obtained with two different plasma samples are shown in FIG. 3. The amount of radioactivity present in each band was estimated and the ratio between the amount of radioactivity present in mutant and the wild type (patient) DNA bands was plotted against the input mutant viral RNA. Using this technique, the amount of viral RNA present in the samples were determined to be 88,000 copies of RNAs per ml of plasma of patient 1 and 16,000 copies of RNAs per ml of plasma of patient 2 (FIG. 3C).

Next the reproducibility of the ICVPCR method was assessed. The amount of viral RNA in a plasma sample was estimated by performing the entire assay on two different days. The amount of RNA by this two estimates were 60000 and 68000 copies per ml of plasma (FIG. 4) demonstrating that the ICVPCR method is reliably reproducible.

Conclusions

Competitive RNA PCR has been successfully used for the estimation of the levels of HIV-1 viral RNA present in patient samples (Piatak et al., *Science* 259:1749–1754 (1993); Clementi et al., *PCR Methods Appl.* 2:191–196 (1993)). In this procedure, the ratio of the amplified products is affected equally by the factors which influence the PCR. However, it lacks a control for the RNA purification step. It has been estimated that on average, 36% of the RNA sample can be lost due to the extraction procedures used (Clementi et al., *PCR Methods Appl.* 2:191–196 (1993)). To account for the variable loss of RNA when gene expression is studied using RNA extracted from cells, the RNA expressed by the gene under study is often compared to another RNA species which is constitutively expressed (Green et al., *Cell* 35:137–148 (1983); Orkin et al., *J. Biol. Chem.* 259:8679–8681 (1984)). However, such a control RNA is not available in plasma. By adopting the modified method described in this report, the mutant virion RNA can sense the role both as a control for the RNA extraction procedure as well as a competitive RNA template in the PCR.

TABLE 1

Oligodeoxyribonucleotide Primer Sequences Used in the PCR

| Primer | Sequence | Position in HIVNL4.3 | SEQ ID NO |
|---|---|---|---|
| ICVPCR-9 | 5' TCCCTGCTTGCCCATACTA 3' | 890–908 (complementary) | SEQ ID NO: 1 |
| ICVPCR-16 | 5' ATCTCTCGACGCAGGACT 3' | 681–698 | SEQ ID NO: 2 |
| ICVPCR-17 | 5' GCTCTCGCACCCATCTCT 3' | 786–803 | SEQ ID NO: 3 |

TABLE 1-continued

Oligodeoxyribonucleotide Primer Sequences Used in the PCR

| Primer | Sequence | Position in HIVNL4.3 | SEQ ID NO |
|---|---|---|---|
| ICVPCR-18 | 5' ACTAGCGGAGGCTAGAAGGA 3' | 765–803 (complementary) | SEQ ID NO: 4 |

All publications cited herein are fully incorporated by reference into the disclosure in their entirety.

From the forgoing it will be appreciated that, although specific embodiments of the invention have been described herein for the purposes of illustration, various modifications may be made without deviating from the spirit and scope of this invention and the following claims. As examples, the steps of the preferred embodiments constitute only one form of carrying out the process in which the invention may be embodied.

What is claimed is:

1. A method for quantitating an amount of a wild type virus present in a sample from a mammal, amphibian, reptile or bird, said method comprising the steps of:
  (a) adding to an aliquot of said sample, as an internal control, a composition comprising a specified amount of a genetically tagged virus containing a genetically tagged nucleic acid having a genetic tag sequence, said genetic tag sequence having a mutation in a region other than a conserved, non-coding region of said wild type virus, said mutation comprising a deletion, insertion or substitution, thereby providing a novel, engineered site having a sequence that does not occur in a genome contained in the sample at a position corresponding to the engineered site;
  (b) co-isolating said wild type nucleic acid and said genetically tagged nucleic acid, respectively, from said wild type virus and said genetically tagged virus in said sample;
  (c) amplifying in vitro said wild type nucleic acid and said genetically tagged nucleic acid from said sample to provide amplified wild type nucleic acid and amplified tagged nucleic acid;
  (d) quantitating the ratio of the amount of said amplified wild type nucleic acid to said amplified tagged nucleic acid provided in said amplifying step (c);
  (e) wherein the ratio of amplified wild type nucleic acid to genetically tagged nucleic acid, quantitated in step (d), is proportional to the ratio of said wild type virus to said genetically tagged virus in said sample, and
  wherein said genetically tagged nucleic acid comprises a genetic tag sequence of sufficient length that said wild type and genetically tagged nucleic acids can be quantitated after amplification, and wherein the genetic tag sequence does not prohibit the growth of said genetically tagged virus.

2. The method of claim 1 wherein said wild type viral nucleic acid is RNA.

3. The method of claim 2 wherein said RNA is retroviral RNA.

4. The method of claim 3 wherein said retroviral RNA is from a virus selected from the group consisting of HTLV-I, HTLV-2, HIV-1 and HIV2.

5. The method of claim 1 wherein said sample is obtained from a mammal.

6. The method of claim 1 wherein said amplifying step (c) comprises reverse transcription.

7. The method of claim 1 wherein said sample is from a member selected from the group consisting of blood, cerebrospinal fluid, saliva, lymphatic tissue, seminal tissue, vaginal tissue, serum, plasma, lymphoid cells, lymphocyte cells, B cells, T cells, monocytes, polymorphonuclear cells, macrophages, epithelial cells, nasopharyngeal epithelium, upper respiratory tract epithelium, labial epithelium, tumor cells, respiratory secretions, nasopharyngeal secretions, brain tissue, virus vesicle tissue, wart tissue, feces, urine, pleural and pericardial fluid, milk, salivary gland tissue, negri body tissue, and hepatic cells.

8. The method of claim 1 wherein said sample comprises blood.

9. The method of claim 1 wherein said sample comprises plasma.

10. The method of claim 1 wherein said genetically tagged virus is a retrovirus.

11. The method of claim 1 wherein said quantitating step (d) further comprises hybridizing at least one hybridization probe with said amplified wild type nucleic acid and said amplified genetically tagged nucleic acid, wherein said hybridization probe is specific for at least one or both of said amplified wild type nucleic acid and said amplified genetically tagged nucleic acid.

12. The method of claim 11 wherein said probe is labeled.

13. The method of claim 1 wherein said quantitating step (d) further comprises separating the amplified wild type nucleic acid from the amplified genetically tagged nucleic acid.

14. The method of claim 13 wherein said separating comprises electrophoresis of said amplified wild type nucleic acid and said amplified genetically tagged nucleic acid.

15. The method of claim 1 wherein said genetic tag sequence comprises an inserted nucleic acid sequence added to the sequence of said wild type nucleic acid.

16. The method of claim 1 wherein said genetic tag sequence comprises a deletion mutation of a sequence of said wild type nucleic acid.

17. The method of claim 1 wherein said genetic tag sequence comprises a point mutation of a sequence of said wild type nucleic acid.

18. The method of claim 1 wherein said genetic tag sequence is 5–50 nucleotides in length.

19. The method of claim 11 wherein said ratio of wild type nucleic acid to genetically tagged nucleic acid is proportional to the relative amounts of probe hybridized to said wild type nucleic acid and said genetically tagged nucleic acid, respectively.

20. The method of claim 1 wherein said quantitating step (d) involves a method selected from the group consisting of labeled nucleotide incorporation, absorption spectroscopy, nucleic acid hybridization, antibody detection and restriction analysis.

* * * * *

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
      (A) LENGTH: 19 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:1:

TCCCTGCTTG CCCATACTA                                          19

(2) INFORMATION FOR SEQ ID NO:2:

(i) SEQUENCE CHARACTERISTICS:
      (A) LENGTH: 18 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:2:

ATCTCTCGAC GCAGGACT                                          18

(2) INFORMATION FOR SEQ ID NO:3:

(i) SEQUENCE CHARACTERISTICS:
      (A) LENGTH: 18 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:3:

GCTCTCGCAC CCATCTCT                                          18

(2) INFORMATION FOR SEQ ID NO:4:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: cDNA -continued (xi) SEQUENCE DESCRIPTION: SEQ ID NO:4:

ACTAGCGGAG GCTAGAAGGA                                              20

(2) INFORMATION FOR SEQ ID NO:5:

(i) SEQUENCE CHARACTERISTICS:
      (A) LENGTH: 25 base pairs
      (B) TYPE: nucleic acid
      (C) STRANDEDNESS: both
      (D) TOPOLOGY: both (ii) MOLECULE TYPE: cDNA (xi) SEQUENCE DESCRIPTION: SEQ ID NO:5:

AGACATCTAG ACGCGTCTAG ACGCG                                        25